United States Patent [19]

Onopchenko et al.

[11] Patent Number: 4,560,721

[45] Date of Patent: Dec. 24, 1985

[54] PROCESS FOR PREPARING AN ETHER SOLUTION OF POLYAMIC ACIDS AND POLYIMIDE RESINS

[75] Inventors: Anatoli Onopchenko, Monroeville; Edward T. Sabourin, Allison Park; Charles M. Selwitz, Monroeville, all of Pa.

[73] Assignee: Gulf Research & Development Company, Pittsburgh, Pa.

[21] Appl. No.: 394,260

[22] Filed: Jul. 1, 1982

[51] Int. Cl.$^4$ .................... C08L 61/00; C08L 77/10
[52] U.S. Cl. ...................... 524/378; 524/600; 528/222; 528/229; 564/329; 568/306
[58] Field of Search ............... 564/153, 329; 568/306; 524/378, 600; 528/222, 229

[56] References Cited

U.S. PATENT DOCUMENTS

| | | | |
|---|---|---|---|
| 3,014,908 | 12/1961 | Coleman et al. | 564/329 X |
| 3,075,007 | 1/1963 | McCracken et al. | 568/306 X |
| 3,175,007 | 3/1965 | Berhenke | 564/329 X |
| 3,869,513 | 3/1975 | Buckman et al. | 568/306 X |
| 3,975,444 | 8/1976 | Kovar et al. | 568/306 X |
| 4,320,217 | 3/1982 | D'Alelio et al. | 564/153 |

OTHER PUBLICATIONS

Degering, An Outline of Organic Nitrogen Compounds, University Lithoprinters, Ypsilanti, Mich. (1950), pp. 295–296.

Primary Examiner—James H. Reamer
Assistant Examiner—Vera C. Clarke

[57] ABSTRACT

A novel ether solution of dinitrobenzophenone and a process for preparing an ether solution of diaminobenzophenone therefrom which comprises subjecting a dinitrobenzophenone dissolved in said ether solvent to hydrogenation in contact with a continuous nickel catalyst to obtain said solution of diaminobenzophenone dissolved in said ether solvent. In a specific embodiment said nickel catalyst is mounted on an inert support. In a still further embodiment, said diaminobenzophenone dissolved in said ether solvent, after removal of water therefrom, is reacted with an aromatic dianhydride to obtain a polyamic acid solution. The polyamic acid solution can be heated at a temperature above 100° C. to drive off water of cyclization and thereby obtain the corresponding polyimide resin.

10 Claims, No Drawings

PROCESS FOR PREPARING AN ETHER SOLUTION OF POLYAMIC ACIDS AND POLYIMIDE RESINS

FIELD OF THE INVENTION

This invention relates to a novel ether solution of dinitrobenzophenone and a process for preparing an ether solution of diaminobenzophenone dissolved in said ether solvent which comprises subjecting a dinitrobenzophenone dissolved in said ether solvent to hydrogenation in contact with a continuous nickel catalyst to obtain said solution of diaminobenzophenone dissolved in said ether solvent.

DESCRIPTION OF PRIOR ART

Dinitrobenzophenones can be subjected to hydrogenation to obtain the corresponding diaminobenzophenones and the latter can be reacted with an aromatic dianhydride to obtain polyamic acids, which can then be heated to drive off water of cyclization and thereby obtain the corresponding polyimide resin.

When dinitrobenzophenones and hydrogenated to obtain the corresponding diaminobenzophenones, unfortunately in some cases underhydrogenation occurs, with the result that some of the nitro groups will not be converted to the corresponding amine groups. In some cases, on the other hand, overhydrogenation will occur, with the result that not only all of the nitro groups will be converted to the corresponding amine groups, but the bridging carbonyl will also be hydrogenated, and a benzhydrol will be obtained. In most cases, however, benzhydrol formation occurs while some of the nitro groups are still unreacted. Thus, we have found that when we carried out the hydrogenation of dinitrobenzophenones using ruthenium as catalyst, incomplete hydrogenation resulted and we obtained poor selectivities. With platinum and palladium it was extremely difficult to stop the reaction after conversion of the nitro groups, and some hydrogenation of the carbonyl bridge occurred, even when the stoichiometric amount of hydrogen was added. Raney nickel, which is pyrophoric, contains large voids and possesses a discontinuous bulk volume, was also used, but the hydrogenation was non-selective, in that the nitro groups and the bridging carbonyl were indiscriminately hydrogenated.

If the hydrogenated product, containing the desired diaminobenzophenone and some of the underhydrogenated analog containing at least one free nitro group and/or the overhydrogenated analog, a benzhydrol, is reacted with an aromatic dianhydride to obtain a polyamic acid polymer, unsatisfactory results will be obtained. The non-hydrogenated nitro group on the benzophenone and/or benzhydrol will act as a chain stopper, and high molecular weight polymers will not be obtained. The presence of the hydroxyl function in the benzhydrol will have a tendency not only to alter the property of the final polymer, but, more important, it will introduce tertiary hydrogens into the polymer, creating weak links in its structure, thereby reducing its thermal stability.

However, if an attempt is made to remove the underhydrogenated and/or overhydrogenated product from the desired diaminobenzophenone by crystallization, handling problems arise, because all diaminobenzophenone isomers, except for the m,p'-isomer, give a positive response to the Ames test, indicating that such amines are potentially carcinogenic and mutagenic to humans. Therefore, it is highly desirable, for health and safety reasons, to avoid handling and isolation of diaminobenzophenones in the solid form. The recovery of diamines by crystallization is economically unattractive, and during isolation a considerable amount of carcinogenic diamines will be left behind in the filtrate, creating a disposal problem.

It would be highly desirable, therefore, for the diaminobenzophenone product to be used to prepare polyamic acids not only to be free of under- and overhydrogenated precursors of diaminobenzophenones, but it would also be desirable to carry out the hydrogenation reaction in a solvent satisfactory in both the hydrogenation stage and in the polymer-forming stage, so that no recovery or handling of the diaminobenzophenone solids is required. Unfortunately, the selection of a suitable solvent gives rise to additional problems. Some solvents, such as ethyl acetate, tetrahydrofuran and p-dioxane, boil at temperatures at about or below the boiling point of water, so that when water from the hydrogenation step is removed from the product, the solvents are removed first. Removal of water thereafter leaves only the solid diaminobenzophenone product behind. If water of reaction is allowed to remain behind in the solution during the polymer-forming stage, the polyamic acids produced on standing will undergo hydrolysis of the amide linkages, and high molecular weight polymers will not be obtained. Hydrolysis has the effect of lowering the inherent viscosity of the polyamic acid solution.

Most solvents, such as ethyl acetate, tetrahydrofuran, p-dioxane, etc., have a tendency to adhere to diaminobenzophenones as solvents of crystallization, which can be removed by simple means, such as heating in a vacuum at an elevated temperature, for color problems arise. For example, diaminobenzophenones carrying p-dioxane of crystallization on heating at 70° C. for 72 hours in a vacuum oven still carried p-dioxane. Heating to 100° C. caused the diaminobenzophenones to go from dark yellow to dark green and finally to black color, without removal of p-dioxane solvent of crystallization. It is clear, therefore, that solvents that are not useful or detrimental in the polymerization step should not be used in the hydrogenation reaction.

SUMMARY OF THE INVENTION

We have found that if a novel ether solution of dinitrobenzophenone is subjected to hydrogenation in contact with a continuous nickel catalyst, a solution of diaminobenzophenone will be obtained containing no appreciable underhydrogenation or overhydrogenation products, the recovery of catalyst and removal of water therefrom are easily effected and handling of diaminobenzophenones as solids will be obviated, since the resulting solution can be used as such for reaction of the diaminobenzophenones therein with an aromatic dianhydride.

In carrying out the process defined and claimed herein, any isomer of dinitrobenzophenone can be used to obtain the corresponding diaminobenzophenone. In a preferred embodiment, however, a mixture of diaminobenzophenones, such as those obtained in our copending application Ser. No. 242,691, filed on Mar. 11, 1981, now U.S. Pat. No. 4,361,704, for Process for Preparing m,m-Dinitrobenzophenone, are used. Thus, in the preferred mixture there will be present m,m'-dinitrobenzophenone and m,p'dinitrobenzophenone in a weight ratio of 90:10 to about 100:0, preferably about 92:8 to about 99:1. If o,m'-dinitrobenzophenone is present, it will be present in amounts up to about 15 weight percent, generally up to about five weight percent, but most often only up to about two weight percent.

In carrying out the hydrogenation step herein, the dinitrobenzophenone or mixture of dinitrobenzophenones are dissolved in an ether solvent whose boiling point at atmospheric pressure must be greater than about 100° C., preferably is in the range of about 120° C. to about 300° C., and which is defined by the following formula:

$$R_1\text{—}O\text{—}(CH_2CH_2O)_n\text{—}R_2,$$

wherein n is an integer from 0 to 4, preferably from 1 to 3; and $R_1$ and $R_2$, the same or different, are alkyl groups, which can be linear or branched, having from one to 10 carbon atoms, preferably from one to five carbon atoms, such as methyl, ethyl, n-propyl, isopropyl, n-butyl, isobutyl, n-amyl, isoamyl, octyl, nonyl, etc. Specific examples of ethers than can be used as solvents herein mentioned can be made of the following:

| | |
|---|---|
| diethylene glycol dimethyl ether (diglyme) | B.P. 162° C.; |
| diethylene glycol diethyl ether, | B.P. 189° C.; |
| triethylene glycol dimethyl ether (triglyme) | B.P. 216° C.; |
| triethylene glycol diethyl ether | B.P. 243° C. |
| tetraethylene glycol dimethyl ether (tetraglyme) | B.P. 275°–276° C.; |
| tetraethylene glycol diethyl ether, | B.P. 300° C.; |
| ethylene glycol diethyl ether, | B.P. 123° C.; |
| di-n-butyl ether | B.P. 141° C.; |
| di-n-amyl ether, | B.P. 187°–188° C.; |
| di-isoamyl ether, | B.P. 172° C.; |
| etc. | |

The selection of the catalytic component of the catalyst for hydrogenation is critical and must be continous elemental nickel itself or nickel oxide, which can be converted to nickel via activation with hydrogen, preferably mounted on an inert support, such as kieselguhr, pumice, diatomaceous earth, kaolin, silica, alumina, magnesia, silica-alumina, etc. Based on the total weight of the catalyst, the nickel or nickel oxide content thereof will be in the range of about 20 to about 70 weight percent, preferably about 40 to about 60 weight percent. The surface area of the supported catalyst (support plus metal) will be, for example, in the range of about 50 to about 300 m²/g but generally will be in the range of about 100 to about 200 m²/g. The catalyst can assume any suitable shape or form, for example, powder, tablet, sphere, etc. The nickel or nickel oxide can be deposited on the support in any suitable or convenient manner. For example, using the incipient wetness technique, the support can be stirred in a nickel nitrate solution and then the support carrying the nickel nitrate can be calcined at temperatures above about 400° C. to convert the nickel nitrate to nickel oxide. Another procedure that can be used involves precipitating nickel oxide or nickel hydroxide on the support by mixing a nickel nitrate solution with the support in the presence of sodium hydroxide. The support then carrying nickel hydroxide can then be calcined as described above. The hydrogenation catalyst used herein, therefore, obviously excludes Raney nickel, which is a porous form of non-supported metallic nickel obtained by reacting nickel aluminum alloys with caustic, such as sodium hydroxide. Thus Raney nickel contains large voids and possesses a discontinous volume, whereas the nickel used herein is continous, in that no appreciable voids are present and the portions forming a part thereof are in intimate contact with each other. The nickel catalyst during hydrogenation will be in the zero valent state.

The hydrogenation of the dinitrobenzophenone is easily carried out by dissolving the dinitrobenzophenone in the defined ether solvent, thus forming the novel ether solution of dinitrobenzophenone, and adding the defined hydrogenation catalyst thereto. If the hydrogenation catalyst requires activation, particularly after long storage periods, or if nickel oxide is used, this is generally done prior to hydrogenation, for example, by adding the catalyst to a solvent, preferably the same ether solvent that will be used in the hydrogenation reaction, and while stirring, bringing the temperature to about 170° to about 220° C., preferably about 190° to about 200° C., under a hydrogen pressure of about 500 to about 1500 psig (about 3.5 to about 10.5 MPa), preferably about 600 to 1000 psig (about 4.2 to about 7.0 MPa) for about 15 minutes to about three hours, preferably about one-half to about one hour. The amount of ether solvent used is such that the amount of dinitrobenzophenone dissolved therein will be in the range of about one to about 40 weight percent, preferably about five to about 30 weight percent. The weight of catalyst, based on the reaction mixture, will be in the range of about 0.25 to about 10 weight percent, preferably about one to about five weight percent. The slurry containing the solvent, the dinitrobenzophenone dissolved therein and the activated catalyst, is stirred while its temperature is raised to about 80° to about 170° C., preferably about 100° to about 150° C. and then pressured with hydrogen to about 50 to about 1200 psig (about 0.3 to about 8.4 MPa), preferably about 200 to about 1000 psig (about 1.4 to about 7.0 MPa). At the end of about one-half to about six hours, but generally about one to about four hours, the hydrogenation reaction is complete and dinitrobenzophenone has been converted to the corresponding diaminobenzophenone with no appreciable amounts of underhydrogenated product containing free nitro groups or overhydrogenated product containing hydroxyl groups, for example, benzhydrols, present.

The hydrogenated product will contain the ether solvent, the diaminobenzophenone, water from the hydrogenation reaction and the dispersed hydrogenation catalyst. The latter can be removed from the hydrogenated product in any convenient manner, for example, by filtration, and reused. Water is removed easily from the remainder of the product, since its boiling point is well below the boiling points of the ether solvent and the diaminobenzophenone product. Thus, the water is simply removed, by heating the product to a temperature above 100° C. at atmospheric pressure, or even lower temperatures when distillation is carried out under vacuum. Other methods of preparing the solution of diaminobenzophenone in other solvents could include distillation first followed by filtration of catalyst, or even passing the entire solution over a column containing drying agents, such as molecular sieves, anhydrous magnesium sulfate, etc. Left behind will be the desired ether solution of diaminobenzophenone.

In a preferred embodiment, the ether solution of diaminobenzophenone obtained above is reacted with an aromatic dianhydride to obtain a polyamic acid solution, which in an even more preferred embodiment is then heated at temperatures above about 100° C. to drive off water of cyclization and thereby obtain the corresponding polyimide resin. Among the aromatic anhydrides that can be used to react with the diaminobenzophenone, mention can be made of pyromellitic dianhydride, benzophenonetetracarboxylic dianhydride (BTDA), methylenebis(Phthalic anhydride) etc. This reaction can be carried out in any desired manner. For example, in one embodiment, approximately stoichiometric amounts of the dianhydride can be added to the defined ether solution of diaminobenzophenone obtained above while permitting the reaction to proceed in an inert atmosphere, such as nitrogen, argon, helium, etc., at a temperature of about 15° to about 75° C., preferably about 20° to about 50° C., and a pressure of about 15 to about 25 psig (about 0.1 to about 0.15 MPa), preferably atmospheric, for about one to about 24 hours, preferably about two to about 10 hours, until the desired viscosity level is reached, for example, about 0.4 to about 1.0 deciliter per gram, indicating that the desired polymerization is reached. The product is a polyamic acid dissolved in the ether solvent. If a cosolvent is needed to aid in solubilization and/or polymerization, additional ether solvents, as defined above, or tetrahydrofuran can be used in the preparation of the polyamic acid solution. The amount of solvent used can vary over a wide range, for example, about 60 to about 99 parts by weight per weight of the total reactants, preferably about 75 to about 95 parts by weight per weight of the total reactants.

Polyimides can be prepared from polyamic acid solution obtained above by merely heating the same to a temperature above about 100° C., preferably about 125° to about 300° C. at atmospheric pressure to drive off water of cyclization and thereby obtain the corresponding polyimide resin.

DESCRIPTION OF PREFERRED EMBODIMENTS

The following will exemplify the novel process defined and claimed herein.

EXAMPLE I

A total of five grams of dinitrobenzophenone (containing 93.5 weight percent m,m'-dinitrobenzophenone and 6.5 weight percent m,p'-dinitrobenzophenone) dissolved in 100 milliliters of ethyl acetate was subjected to hydrogenation in a Parr shaker in contact with 0.44 gram of catalyst carrying five weight percent of palladium on carbon at 25° C. and in an hydrogen atmosphere of 50 to 60 psig (0.3 to 0.4 MPa) until 88 psig of hydrogen were taken up (calculated theoretical value=100 psig). The yellowish solid-liquid mixture was heated to about 60° C. to dissolve the product, the solution was filtered to separate the product from the catalyst, and the filtrate was evaporated to dryness to give 5.3 grams of diaminobenzophenone carrying one mol of ethyl acetate of crystallization.

A total of 2.65 of the above product was dissolved in equal amounts by weight of diglyme and tetrahydrofuran to form a 15 weight percent solids solution, which was then treated with an equal molar amount of benzophenone tetracarboxylic dianhydride. No viscosity build-up was evident after six hours; therefore, no polymer was formed.

Analysis of the remaining product by NMR and high pressure liquid chromatography (HPLC) showed that only about 95 percent of the nitro groups on the dinitrobenzophenone charge had been converted to amine. At the same time, a small, but detectable, amount of benzhydrol structure was also evident by NMR analysis. Obviously, this is an indication that with the catalyst used, some overhydrogenation occurred, while some of the nitro groups remained unreacted.

The remaining 2.5 grams of the crude diamine was recrystallized from twice its weight with a 60:40 weight mixture of acetic acid and acetone to give 0.92 gram of a first crop of solids and 0.74 gram of a second crop of solids. Analyses by HPLC showed both fractions to be identical and that only m,m'-diaminobenzophenone was present. It appears that both overhydrogenated and underhydrogenated product remained in the solution, as well as the m,p'-diaminobenzophenone isomer.

EXAMPLE II

A total of five grams of the same dinitrobenzophenone used in Example I dissolved in 100 milliliters of isopropanol was subjected to hydrogenation in a Parr shaker in contact with 0.2 gram of catalyst carrying 10 weight percent of palladium on carbon at 25° C. and in a hydrogen atmosphere at 50 to 60 psig (0.3 to 0.4 MPa) until 77 psig of hydrogen were taken up. No further hydrogen uptake was noted after an additional two hours. The theoretical uptake of hydrogen was 100 psig. It appears that the diamine being formed recrystallized out of solution, coated the catalyst, and reaction stopped at only 80 percent conversion level. It might appear that higher temperature might help the solubility problem, but one discouraging aspect resided in the fact that some benzhydrol structure was already present, and a considerable number of nitro groups remained unreacted.

EXAMPLE III

A total of 4.2 grams of the same dinitrobenzophenone used in Examples I and II dissolved in 100 milliliters of acetic acid was subjected to hydrogenation in a Parr shaker in contact with 0.5 gram of catalyst carrying 10 weight percent palladium on carbon at 50° C. and in a hydrogen atmosphere at 50 to 60 psig (0.3 to 0.4 MPa). The reaction rapidly took up hydrogen initially, but quickly slowed down. After 11 hours only 75 percent of the theoretical hydrogen was consumed, and then reaction stopped. It appears that this catalyst in acetic acid was poisoned by the amine that had formed.

EXAMPLE IV

A total of 10 grams of dinitrobenzophenone, of which 87.3 weight percent of m,m'-dinitrobenzophenone and the remainder was 5.7 weight percent m,p'-dinitrobenzophenone and 7.0 weight percent was o,m'-dinitrobenzophenone, was hydrogenated in a one-liter autoclave containing two grams of Raney nickel at 50° C. and a hydrogen pressure of 400 psig (2.8 MPa). A total of 70 psig of hydrogen was consumed in two hours. Analysis of the reaction mixture showed the reaction to be incomplete and the catalyst appeared to be poisoned.

The above solution was heated to 65° C. to dissolve the solids and then filtered. The filtrate was evaporated to dryness to give 8.54 grams of residue. This residue was transferred to a Parr shaker, diluted with 100 milliliters of ethyl acetate and further hydrogenated, using two grams of fresh Raney nickel, as above, until 57 psig of hydrogen were consumed. Analysis by HPCL and NMR of the final product, amounting to eight grams, showed some overhydrogenation (benzhydrols) as well as some free nitro groups. Raney nickel therefore is a non-selective catalyst for the conversion of dinitrobenzophenone solely to diaminobenzophenone.

EXAMPLE V

Example IV was repeated using only five grams of the dinitrobenzophenone charge in 100 milliliters of ethyl acetate at 55° C. and under a hydrogen pressure of 50 to 60 psig (0.3 to 0.4 MPa) until the theoretical amount of hydrogen was consumed. Unfortunately, the desired selectivity was not obtained, since both underhydrogenation and overhydrogenation of dinitrobenzophenone occurred.

EXAMPLE VI

A total of 10 grams of the same dinitrobenzophenone used in Examples I to III dissolved in 350 milliliters of p-dioxane was subjected to hydrogenation in a one-liter autoclave in contact with 2.4 grams of commercial nickel catalyst carrying 58 weight percent of nickel on kieselguhr (surface area of 160 m$^2$/g) at 148° C. and in a hydrogen atmosphere at 1000 psig (7.0 MPa). A total of 90 psig of hydrogen was consumed in one hour. The autoclave was cooled to room temperature, depressured and the contents were filtered to separate catalyst from the product solution. Evaporation of the filtrate to dryness gave eight grams of pale yellowgreen solids, corresponding in composition to diaminobenzophenone carrying p-dioxane of crystallization. The isolated product corresponded to a 90 percent yield. Treatment of the crude product in boiling water, filtering and then recovering the precipitated product resulted in pure m,m'-diaminobenzophenone, melting point 151°–152° C., free of p-dioxane after drying in a vacuum oven for 48 hours at 70° C.

EXAMPLE VII

A total of 50 grams of the same dinitrobenzophenone charge used in Examples I to III dissolved in 400 milliliters of ethyl acetate were subjected to hydrogenation over four grams of nickel (58 weight percent nickel on kieselguhr) catalyst at 140° C. and a hydrogen pressure of 500 psig (3.5 MPa) over a period of one hour. A total of 650 psig of hydrogen were consumed. On workup 36.7 grams of solids were obtained containing 10 weight percent of ethyl acetate of crystallizaton. The isolated yield corresponded to 85 percent. Some of the product adhered to the catalyst but was not recovered.

EXAMPLE VIII

A total of 10 grams of the same dinitrobenzophenone charge used in Examples I to III dissolved in 50 milliliters of diglyme were subjected to hydrogenation in a Parr shaker over 0.5 grams of catalyst composed of 10 weight percent palladium on carbon at 50° C. to 60° C. and a hydrogenation pressure of 50 to 60 psig (0.3 to 0.4 MPa) until the theoretical amount of hydrogen was consumed. Analysis of the product showed it consisted of 88.8 weight percent m,m'-diaminobenzophenone, 4.7 weight percent m,p-diaminobenzophenone, 2.8 weight percent unreacted dinitrobenzophenone, and 3.7 weight percent benzhydrol derivatives.

EXAMPLE IX

Example VIII was repeated except that five weight percent of the catalyst was used with ethyl acetate as solvent. The hydrogenation temperature was maintained at 25° C. and the pressure at 50 to 60 psig (0.3 to 0.4 MPa). Although the theoretical amount of hydrogen was consumed, both overhydrogenation and underhydrogenation products were present in the final product.

EXAMPLE X

Example IX was repeated using two grams of a ruthenium catalyst containing five weight percent of ruthenium on carbon. The solvent was isoproponal and the temperature 50° C. In this case, only 70 percent of the theoretical amount of hydrogen was consumed, indicating, perhaps, catalyst poisoning.

EXAMPLE XI

A total of 50 grams of dinitrobenzophenone, assay 96.5 weight percent of which 94 percent was m,m'-dinitrobenzophenone and six weight percent was the m,p'-isomer, dissolved in 400 milliliters of tetrahydrofuran was subjected to hydrogenation in a one-liter autoclave in contact with eight grams of nickel catalyst at a temperature of 150° C. and a hydrogenation pressure of 500 psig (3.5 MPa) until the reaction stopped. On workup, as before, 40.2 grams of diaminobenzophenone were obtained containing nine weight percent of tetrahydrofuran of crystallization.

EXAMPLE XII

A total of 40 grams of dinitrobenzophenone, of which 94 weight percent was m,m'-dinitrobenzophenone and four weight percent was m,p'-dinitrobenzophenone was charged to a one-liter stainless steel autoclave along with five grams of Ni 104 P catalyst in 400 milliliters of diglyme. The catalyst had previously been activated in tetrahydrofuran at 200° C. and a hydrogen pressure of 1000 psig (7.0 MPa) for one-half hour. The autoclave was purged with hydrogen and the temperature was brought to 140° C. while the contents were vigorously stirred. The pressure was brought to 1000 psig (7.0 MPa) and maintained between 800 and 1000 psig (5.6 to 7.0 MPa) until hydrogen was no longer consumed, which required about one hour. The total pressure drop of 700 psig is consistent with the stoichiometric reduction of two nitro groups on all of the dinitrobenzophenone. the autoclave was discharged and the catalyst removed from the hydrogenation product by filtration. The water of hydrogenation and much of the diglyme were removed from the product by distillation at around 15 millimeters of mercury and 44°–46° C. The total residue weighing 178 grams contained 30.08 grams of diaminobenzophenone and 147.92 grams of diglyme. A total of 148.8 grams of tetrahydrofuran was added to the residue, resulting in a weight ratio of 1:1 of diglyme and tetrahydrofuran in the resulting mixture. The mixture was maintained at 40° to 50° C. to prevent crystallization of diaminobenzophenone. A 28-gram aliquot, containing 2.58 grams, or 0.0121 mol of diaminobenzophenone, was placed in a 100-milliliter flask under a nitrogen atmosphere. To this over a period of 0.5 hour there was added by way of a screw feeder a total of 3.9 grams (0.0121 mol) of benzophenone tetracarboxylic dianhydride. The resulting mixture was permitted to stir overnight at room temperature. Determination of the inherent viscosity of the resulting polyamic acid solution in dimethylacetamide solution gave a value of 0.6 deciliter per gram. Solutions of similar viscosity have been shown to provide adequate resin properties. Analysis of the final polyamic acid solution for the presence of diaminobenzophenone by HPLC showed that no free amine was present.

The results obtained above are surprising. In none of Examples I, II, III, IV, V, VIII and IX, wherein neither the ether solvent of choice nor the nickel catalyst of choice was used, were satisfactory results obtained, for in each case, over- and/or underhydrogenation of dinitrobenzophenone occurred, which required isolation of diamine for purification. Water of hydrogenation could not be removed without removing all of the solvent or the product could not be obtained without association with the solvent of crystallization. Even when the nickel of choice was used, but not with the defined solvent, in Examples VI and X, unsatisfactory results were obtained, for the product obtained was associated with solvent of crystallization, and water could not be readily removed from the product. Even when the solvent of choice was used, but without the defined catalyst herein, the product obtained was both under- and overhydrogenated. Only in Example XII, wherein the operation was carried out following the dictates of the claimed process was a solution obtained containing only the desired diaminobenzophenones.

Obviously, many modifications and variations of the invention, as hereinabove set forth, can be made without departing from the spirit and scope thereof, and therefore only such limitations should be imposed as are indicated in the appended claims.

We claim:

1. A process for the preparation of a solution of an ether solvent having a boiling point at atmospheric pressure greater than about 100° C. and having the following formula:

$$R_1-O-(CH_2CH_2O)_n-R_2,$$

wherein n is an integer from 0 to 4 and $R_1$ and $R_2$ are alkyl radicals having from 1 to 10 carbon atoms and a diaminobenzophenone, which comprises subjecting a dinitrobenzophenone dissolved in said ether solvent to hydrogenation in contact with a continuous nickel catalyst to obtain said solution of diaminobenzophenone dissolved in said ether solvent, and reacting the solution of diaminobenzophenone with an aromatic dianhydride to obtain a polyamic acid solution.

2. The process of claim 1 wherein said reaction is carried out at a temperature of about 15° to about 75° C.

3. The process of claim 1 wherein said reaction is carried out at a temperature of about 20° to about 50° C.

4. The process of claim 1 wherein said process is carried out in the additional presence of a cosolvent.

5. The process of claim 1 wherein said cosolvent is tetrahydrofuran.

6. A process for the preparation of a solution of an ether solvent having a boiling point at atmospheric pressure greater than about 100° C. and having the following formula:

$$R_1-O-(CH_2CH_2O)_n-R_2,$$

wherein n is an integer from 0 to 4 and $R_1$ and $R_2$ are alkyl radicals having from 1 to 10 carbon atoms and a diaminobenzophenone, which comprises subjecting a dinitrobenzophenone dissolved in said ether solvent to hydrogenation in contact with a continuous nickel catalyst to obtain said solution of diaminobenzophenone dissolved in said ether solvent, removing said catalyst and water from the hydrogenation product, and reacting the solution of diaminobenzophenone with benzophenone tetracarboxylic dianhydride to obtain a polyamic acid solution.

7. A process which comprises subjecting a dinitrobenzophenone dissolved in an ether solvent to hydrogenation in contact with a continuous nickel catalyst to obtain a solution of diaminobenzophenone dissolved in said ether solvent, said ether solvent having a boiling point at atmospheric pressure greater than about 100° C. and having the following formula:

$$R_1-O-(CH_2CH_2O)_n-R_2,$$

wherein n is an integer from 0 to 4 and $R_1$ and $R_2$ are alkyl radicals having from one to 10 carbon atoms, removing said catalyst and water from the hydrogenation product, reacting the ether solution of diaminobenzophenone with an aromatic dianhydride to obtain a polyamic acid solution, and heating said polyamic acid solution to a temperature above about 100° C. to obtain the corresponding polyimide resin.

8. The process of claim 7 wherein said polyamic acid solution is heated to a temperature of about 125° to about 300° C. to obtain the corresponding polyimide resin.

9. The process of claim 7 wherein said aromatic dianhydride is benzophenone tetracarboxylic dianhydride.

10. The process of claim 9 wherein said polyamic acid solution is heated to a temperature of about 125° to about 300° C. to obtain the corresponding polyimide resin.

* * * * *